United States Patent
Neuwels et al.

(10) Patent No.: US 7,365,097 B2
(45) Date of Patent: Apr. 29, 2008

(54) USE OF AT LEAST ONE (DIHYDRO)JASMONIC ACID DERIVATIVE AS A DESQUAMATING AGENT

(75) Inventors: Michel Neuwels, Waterloo (BE); Maria Dalko, Gif S/Yvette (FR)

(73) Assignee: L'Oreal, S.A., Paris (FR)

( * ) Notice: Subject to any disclaimer, the term of this patent is extended or adjusted under 35 U.S.C. 154(b) by 406 days.

(21) Appl. No.: 10/899,398

(22) Filed: Jul. 27, 2004

(65) Prior Publication Data
US 2005/0063999 A1 Mar. 24, 2005

Related U.S. Application Data

(60) Provisional application No. 60/501,838, filed on Sep. 11, 2003.

(30) Foreign Application Priority Data
Jul. 28, 2003 (FR) .................. 03 09233

(51) Int. Cl.
*A01N 37/08* (2006.01)
*A01N 37/10* (2006.01)
*A01N 37/00* (2006.01)
*A61K 8/18* (2006.01)

(52) U.S. Cl. ............... 514/530; 514/529; 514/715; 424/70.1

(58) Field of Classification Search ............ 514/25, 514/159, 530
See application file for complete search history.

(56) References Cited

U.S. PATENT DOCUMENTS

| 5,861,532 A | 1/1999 | Brown et al. |
|---|---|---|
| 7,098,189 B2 * | 8/2006 | Malik ................ 514/25 |
| 2002/0034524 A1 * | 3/2002 | Poret .................. 424/401 |
| 2003/0224024 A1 | 12/2003 | Leveque et al. |
| 2004/0029839 A1 | 2/2004 | Boulle et al. |

FOREIGN PATENT DOCUMENTS

| EP | 0 585 104 | 3/1994 |
|---|---|---|
| EP | 1 333 021 A2 | 8/2003 |
| EP | 1 333 022 A2 | 8/2003 |
| GB | 1 353 574 | 5/1974 |
| JP | A S48 064054 | 9/1973 |
| WO | WO 93/10756 | 6/1993 |

OTHER PUBLICATIONS

Solomon et. al., Clinics In Dermatology, 1996, 14, 95-99.*
Dave R., et. al. Amino Acids, 24, 2003, 245-261.*
Patent Abstract from Patent Abstracts of Japan for JP A 2001 031552, published Jul. 24, 2001.
Patent Abstract from Patent Abstracts of Japan for JP A 2001 199832, published Feb. 6, 2001.
Office Action from the Japanese Patent Office for Japanese Patent Application No. 2004-219010 (counterpart to U.S. Appl. No. 10/899,398), dated Dec. 2, 2005.
English language Derwent Abstract of EP 1 333 021 A2, published Aug. 6, 2003.
English language Derwent Abstract of EP 1 333 022 A2, published Aug. 6, 2003.
French Search Report for FR 03 09233 (Priority Application for U.S. Appl. No. 10/899,398) dated May 3, 2004.

* cited by examiner

*Primary Examiner*—Shaojia Anna Jiang
*Assistant Examiner*—Roy P Issac
(74) *Attorney, Agent, or Firm*—Finnegan, Henderson, Farabow, Garrett & Dunner L.L.P.

(57) ABSTRACT

Disclosed herein is the cosmetic use, as a desquamating agent, of at least one (dihydro)jasmonic acid derivative of a given formula.

Further disclosed herein is a cosmetic method for smoothing the visible and/or tactile irregularities of the skin surface, for example, for smoothing wrinkles and fine lines and/or skin spots and/or smoothing the skin, comprising topically applying, to the skin, a composition comprising, in a physiologically acceptable medium, at least one (dihydro)jasmonic acid derivative and glycerine.

Other embodiments disclosed herein are novel (dihydro) jasmonic acid derivatives.

6 Claims, No Drawings

USE OF AT LEAST ONE (DIHYDRO)JASMONIC ACID DERIVATIVE AS A DESQUAMATING AGENT

This application claims benefit of U.S. Provisional Application No. 60/501,838, filed Sep. 11, 2003.

Disclosed herein is the use of at least one (dihydro) jasmonic acid derivative as a desquamating agent.

Further disclosed herein is a cosmetic method for smoothing the visible and/or tactile irregularities of the skin surface, for example for smoothing wrinkles and fine lines and/or skin spots and/or smoothing the skin, comprising topically applying, to the skin, a composition comprising, in a physiologically acceptable medium, at least one such (dihydro) jasmonic acid derivative and glycerine.

Desquamation is a natural phenomenon linked to the fact that the epidermis, which constitutes the top layer of the skin, is in constant regeneration. The epidermis comprises several strata of cells, of which the deepest is the basal stratum comprising undifferentiated cells. Over time, these cells will differentiate and migrate to the surface of the epidermis, constituting the various strata thereof, as far as forming, at the surface of the epidermis, the corneocytes, which are dead cells removed by desquamation. This surface loss is compensated for by the migration of cells from the basal stratum to the surface of the epidermis. A forced removal of the horny layer may accelerate renewal and make it possible to improve the quality of the skin surface.

Various agents intended to accelerate renewal of the epidermis are known in the prior art.

The desquamating properties of α-hydroxy acids such as lactic acid, glycolic acid or citric acid, and of β-hydroxy acids, and, for example, salicylic acid and its derivatives (see WO A 93/10756), are thus known.

All of these compounds act against skin aging by promoting desquamation, that is to say the removal of the dead cells situated at the surface of the horny layer of the epidermis. This "desquamating" property is also called, often incorrectly, keratolytic property.

However, the compounds known in the prior art may also have side effects such as tingling, tightness, chafing, and/or red blotches, which may be unpleasant for the user.

It is therefore observed that the need still exists for desquamating agents having an action which is at least as effective as that of the prior art compounds, but which does not exhibit their disadvantages.

One aim of the present disclosure is to overcome these disadvantages of the prior art and to provide novel compounds, derived from (dihydro)jasmonic acid derivatives, capable of promoting desquamation of the skin and/or of stimulating epidermal renewal, the use of which may not cause tingling, tightness, chafing, and/or red blotches which may be unpleasant for the user.

It is known from Japanese patent application JP 2001/199832 to use methyl dihydrojasmonate as a desquamating agent by activating the proteases of the horny layer, such as in the treatment of dry skins. Other jasmonic acid derivatives in which the oxo functional group is replaced by an alcohol functional group (see French patent FR 2 835 525) or comprises an unsaturated side chain (see French patent FR 2 835 526) are also known as desquamating agents.

However, to the knowledge of the present inventors, it has never yet been suggested that other compounds derived from (dihydro)jasmonic acid could be useful as desquamating agents.

These compounds are already known, as prosebogenic agents (see French patent application FR 03/01146, unpublished), in the sense that they may increase the production of sebum by the sebocytes and thus combat hormonal skin drying, which may affect perimenopausal women.

It is, however, not mentioned in this document that the compounds disclosed may also have desquamating role, which may make it possible to envisage their use in cosmetic compositions intended for treating cutaneous signs other than oligoseborrhoeic dry skin.

In addition, in French patent application FR 03/01146, it is not suggested to use these compounds in compositions comprising glycerine.

One embodiment disclosed herein is thus the cosmetic use, as a desquamating agent, of at least one (dihydro) jasmonic acid derivative chosen from the compounds of formula (I):

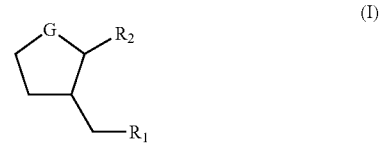

in which:

G is a group chosen from the groups: CH—ORa, CH—NRR', C=CRbRc, CH—CHRR', CYY',

wherein:

Ra is chosen from:
saturated or unsaturated, linear, branched or cyclic $C_1$-$C_{12}$ hydrocarbon radicals optionally substituted with one to five groups, which may be identical or different, chosen from —OR", —OCOR", —SR", —SCOR", —NR"R"', —NHCOR", halogen atoms, —CN, —COOR", and —COR", wherein R" and R"', independently of each other, are chosen from hydrogen, aryl radicals, and saturated or unsaturated, linear or branched hydrocarbon radicals having 1 to 4 carbon atoms; and radicals —CO-Rd wherein Rd is chosen from saturated or unsaturated, linear or branched alkyl, aryl, aralkyl, and alkoxy groups having 1 to 17 carbon atoms, optionally substituted with at least one group chosen from hydroxyl and methoxy groups; Rb and Rc, independently of each other, are chosen from R groups and —COORe groups wherein Re is a $C_1$-$C_4$ hydrocarbon radical;

R and R', independently of each other, are chosen from hydrogen and saturated or unsaturated, linear, branched or cyclic $C_1$-$C_{12}$ hydrocarbon radicals optionally substituted with one to five groups, which may be identical or different, chosen from —OR", —OCOR", —SR", —SCOR", —NR"R"', —NHCOR", halogen atoms, —CN, —COOR", and —COR", wherein R"and R"', independently of each other, are chosen from hydrogen, aryl radicals, and saturated or unsaturated, linear or branched hydrocarbon radicals having 1 to 4 carbon atoms, or R and R' form a ring with the atom to which they are attached;

the dotted line in the structure

represents a saturated or unsaturated divalent hydrocarbon radical having 2 to 3 carbon atoms, optionally substituted with at least one radical chosen from $C_1$-$C_6$ alkyl radicals and aryl radicals;

X and X', independently of each other, are chosen from saturated or unsaturated hydrocarbon radicals having 1 to 3 carbon atoms;

Y and Y' are chosen from halogen atoms, which may be identical or different;

$R_1$ is a radical chosen from —COOR, —CONRR', —$CH_2OR$, —COR, —$CH_2R'$, —$SO_2OR$, —$PO_3RR'$, —NHR and —NRR' radicals wherein R and R' have the meaning indicated above;

$R_2$ is chosen from saturated or unsaturated, linear, branched or cyclic $C_1$-$C_{18}$ hydrocarbon radicals optionally substituted with 1 to 5 groups, which may be identical or different, chosen from —OR", —OCOR", —SR", —SCOR", —NR"R'", —NHCOR", halogen atoms, —CN, —COOR", and —COR", wherein R" and R'" have the meaning indicated above, and the isomers, stereoisomers, and salts thereof.

According to one embodiment disclosed herein, the compound of formula (I) is such that G denotes a group CH—ORa wherein Ra is a linear or branched $C_1$-$C_6$ hydrocarbon radical optionally substituted with at least one group chosen from —OH, —COOH, and —$NH_2$, which may be identical or different; $R_1$ is a radical —COOR wherein R is chosen from a hydrogen atom and unsubstituted, saturated or unsaturated, linear, branched or cyclic $C_1$-$C_{12}$ hydrocarbon radicals; and $R_2$ is chosen from unsubstituted, saturated or unsaturated, linear or branched hydrocarbon radicals having 5 carbon atoms.

The compounds corresponding to the above definition, in which Ra is chosen from monohydroxylated, polyhydroxylated, monocarboxylated, and polycarboxylated radicals, may be prepared according to a two-stage method, according to the following reaction scheme:

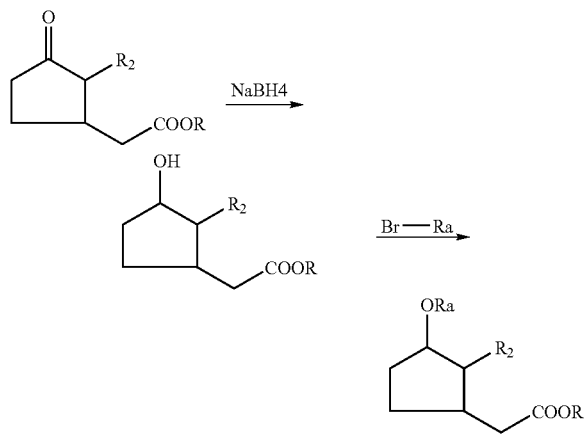

According to this method, the carbonyl functional group of the dihydrojasmonate is reduced in absolute ethanol with sodium borohydride. The alcohol thus formed is then alkylated (using sodium hydride as base, in the case of hydroxylated compounds) in anhydrous DMF, in the presence of the brominated alkylating agent.

In the case where Ra comprises an amine functional group, on the alkylating agent used in the second step of the method above, the amine functional group may be protected in the form of a phthalimide group, the amine functional group then being deprotected with hydrazine in ethanol, as described, for example, in J. Org. Chem., 43, 2320 (1978).

According to another embodiment, the compound of formula (I) is such that G denotes a group CH—NRR' wherein R and R', independently of each other, are chosen from hydrogen and unsubstituted, saturated or unsaturated, linear, branched or cyclic $C_1$-$C_{12}$ hydrocarbon radicals; $R_1$ is a radical —COOR wherein R is chosen from hydrogen and unsubstituted, saturated or unsaturated, linear, branched or cyclic $C_1$-$C_{12}$ hydrocarbon radicals; and $R_2$ is chosen from unsubstituted, saturated or unsaturated, linear or branched hydrocarbon radicals having 5 carbon atoms, wherein the radicals R of G and of $R_1$ may be identical or different.

These compounds may be prepared according to the following reaction scheme:

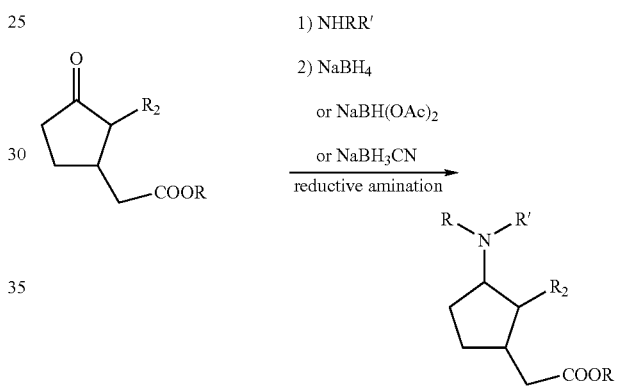

according to methods described for example in S. Bhattacharyya, *Synlett,* 1999, 11, 1781-1783; S. Bhattacharyya, M. P. Cava, *Tetrahedron Lett,* 1964, 2813; H. Speitzer, *Tetrahedron,* 1989, 45, 22, 6999; S. C. Mayer, *Synthetic Comm,* 1994, 24, 16, 2351-2365; B. M. Adger, *Synthesis,* 1987, 53; E. G. Brown, *Tetrahedron Left,* 1997, 38, 49, 8457-8460; U.S. Pat. No. 5,861,532; J. E. Macor, *Heterocycles,* 1990, 31, 8, 1497-1504; and A. P. Kozikowski, *J. Org. Chem.,* 1983, 48, 1000.

According to another embodiment, the compound of formula (I) is such that G is a group CH—ORa wherein Ra is a radical —CO-Rd, wherein Rd is chosen from saturated or unsaturated, linear or branched alkyl, aryl, aralkyl and alkoxy groups, having 1 to 17 carbon atoms, optionally substituted with at least one group chosen from hydroxyl and methoxy groups.

These compounds may be prepared according to the following reaction scheme:

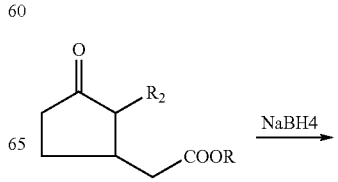

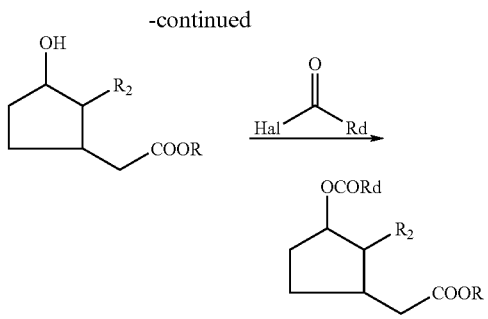

according to a method comprising, in a first step, reacting the corresponding (dihydro)jasmonate with sodium borohydride and, in a second step, bringing the alcohol derivative obtained into contact with the acyl chloride Hal-CO-Rd wherein Hal is chosen from halogen atoms, such as chlorine and bromine, in triethanolamine or pyridine.

According to yet another embodiment, the compound of formula (I) is such that G denotes a group CYY' wherein Y and Y' are chosen from halogen atoms which may be identical or different.

These compounds may be synthesized as described, for example in *Journal of Organic Chemistry*, 45, 14 (1980), by reacting the corresponding dihydrojasmonate with $Et_2NSF_3$ (DAST).

Examples of compounds for use as disclosed herein may be chosen from the compounds of formula (I) such that:

G is chosen from the groups: CH—$OCH_3$, CH—O—$CH_2$—COOH, CH—O—$CH_2$—$CH_2$—$NH_2$, and CH—O—$CH_2$—CH(OH)—$CH_2$OH; $R_1$ is a radical —COOR; and $R_2$ is an n-pentyl radical; for example, G is a group CH—O—CH2-COOH; $R_1$ is a radical COOH; and $R_2$ is an n-pentyl radical;

G is a group CH—OH; $R_1$ is a radical COO—$CH_2$—CHOH—$CH_2$OH; and $R_2$ is an n-pentyl radical;

G is a group $CF_2$; $R_1$ is a radical —COOR; and $R_2$ is an n-pentyl radical;

G is a group CH—N—$(CH_3)_2$; $R_1$ is a radical —COOR, for example a radical chosen from —COOH and —COO—$CH_3$ radicals; and $R_2$ is an n-pentyl radical;

G is chosen from CH—$NH_2$ groups and CH—$NHCH_3$ groups; $R_1$ is a radical-COOH;

G is chosen from CH—O—CO—$CH_2CH_3$ and CH—O—CO—($C_6H_4$OH) groups, and the cosmetically acceptable isomers, stereoisomers, and salts thereof.

As some of the compounds described above are novel, the instant disclosure also relates to these novel compounds.

For instance, one embodiment disclosed herein is at least one (dihydro)jasmonic acid derivative, chosen from the compounds of formula (II):

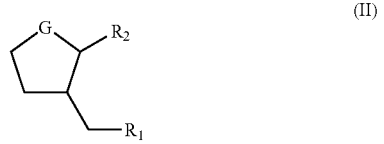

in which:

G is a group chosen from CH—ORa, C=CRbRc, and CYY', wherein:

Ra is a radical —CO-Rd wherein Rd is chosen from saturated or unsaturated, linear or branched alkyl, aryl, aralkyl, and alkoxy groups having 2 to 17 carbon atoms, optionally substituted with at least one group chosen from hydroxyl and methoxy groups;

Rb is a group —COORe wherein Re is a $C_1$-$C_4$ hydrocarbon radical;

Rc is chosen from hydrogen and saturated or unsaturated, linear, branched or cyclic $C_1$-$C_{12}$ hydrocarbon radicals, optionally substituted with one to five groups, which may be identical or different, chosen from —OR", —OCOR", —SR", —SCOR", —NR"R'", —NHCOR", halogen atoms, —CN, —COOR", and —COR", wherein R" and R'", independently of each other, are chosen from hydrogen, aryl radicals, and saturated or unsaturated, linear or branched hydrocarbon radicals having 1 to 4 carbon atoms;

Y and Y' are chosen from halogen atoms, which may be identical or different;

$R_1$ is a radical chosen from —COOR, —CONRR', —$CH_2$OR, —COR, —$CH_2$R', —$SO_2$OR, —$PO_3$RR', —NHR, and —NRR' radicals, wherein R and R', independently of each other, are chosen from hydrogen and saturated or unsaturated, linear, branched or cyclic $C_1$-$C_{12}$ hydrocarbon radicals optionally substituted with one to five groups, which may be identical or different, chosen from —OR", —OCOR", —SR", —SCOR", —NR"R'", —NHCOR", halogen atoms, —CN, —COOR", and —COR", wherein R" and R'", independently of each other, are chosen from hydrogen, aryl radicals, and saturated or unsaturated, linear or branched hydrocarbon radicals having 1 to 4 carbon atoms;

$R_2$ is chosen from saturated or unsaturated, linear, branched or cyclic $C_1$-$C_{18}$ hydrocarbon radicals optionally substituted with 1 to 5 groups, which may be identical or different, chosen from —OR", —OCOR", —SR", —SCOR", —NR"R'", —NHCOR", halogen atoms, —CN, —COOR", and —COR", wherein R" and R'" have the meaning indicated above, and the isomers, stereoisomers, and salts thereof.

As examples of such compounds, mention may be made of the compounds of formula (II) in which G is a group —$CF_2$; $R_1$ is a radical —COOR; and $R_2$ is an n-pentyl radical; and the compound of formula (II) in which G is a group chosen from —CH—O—CO—$CH_2CH_3$ and —CH—O—CO—($C_6H_4$)OH groups; $R_1$ is a radical —COOR; and $R_2$ is an n-pentyl radical.

Another embodiment disclosed herein is also at least one (dihydro)jasmonic acid derivative, chosen from the compounds of formula (III):

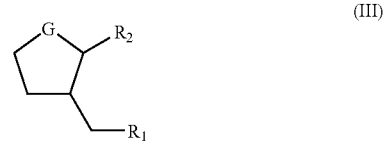

in which:

G is a group —CH—OR', wherein R' is a linear or branched $C_1$-$C_6$ hydrocarbon radical substituted with at least one group chosen from —OH, —COOH, and —$NH_2$, which may be identical or different;

$R_1$ is a radical —COOR, wherein R is chosen from hydrogen and unsubstituted, saturated or unsaturated, linear, branched or cyclic $C_1$-$C_{12}$ hydrocarbon radicals; and $R_2$ is chosen from saturated or unsaturated, linear, branched or cyclic $C_1$-$C_{18}$ hydrocarbon radicals optionally substituted with 1 to 5 groups, which may be identical or different, chosen from —OR", —OCOR", —SR", —SCOR", —NR"R'", —NHCOR", halogen atoms, —CN, —COOR", and —COR", wherein R" and R'", independently of each other, are chosen from hydrogen, aryl radicals, and saturated or unsaturated, linear or branched hydrocarbon radicals having 1 to 4 carbon atoms;

and the isomers, stereoisomers and salts thereof.

As examples of compounds of formula (III), mention may be made of those for which G is a group chosen from: —CH—O—CH$_2$—COOH, —CH—O—CH$_2$—CH$_2$—NH$_2$, and —CH—O—CH$_2$—CH(OH)—CH$_2$OH groups; $R_1$ is a radical —COOR; and $R_2$ is an n-pentyl radical.

An example of such a compound is such that G is a group CH—O—CH$_2$—COOH; $R_1$ is a radical COOH; and $R_2$ is an n-pentyl radical.

Another embodiment disclosed herein is a composition comprising, in a physiologically acceptable medium, at least one compound chosen from formulae (II) and (III) as defined above.

In certain embodiments, this composition is suitable for topical application to the skin and/or the scalp.

Also disclosed herein is a cosmetic method for smoothing the visible and/or tactile irregularities of the skin surface, for example for smoothing the wrinkles and fine lines and/or the skin spots and/or smoothing the skin, comprising topically applying, to the skin, a composition comprising, in a physiologically acceptable medium, at least one (dihydro)jasmonic acid derivative of formula (I), as defined above, and glycerine.

The composition as disclosed herein may be applied to the skin of human subjects having a sufficient sebum production, that is to say a sebum level on the forehead greater than 100 µg/cm$^2$.

The composition is generally suitable for topical application to the skin, and it therefore comprises a physiologically acceptable medium, that is to say a medium which is compatible with the skin and possibly with its superficial body growths (i.e., eyelashes, nails, hair) and/or the mucous membranes.

The quantity of the at least one (dihydro)jasmonic acid derivative which can be used as disclosed herein of course depends on the desired effect and can therefore vary to a great extent. To give an order of magnitude, it is possible to use the at least one (dihydro)jasmonic acid derivative in an amount ranging from 0.01% to 20% of the total weight of the composition, for example in an amount ranging from 0.1% to 10% of the total weight of the composition and, for example, in an amount ranging from 0.5% to 5% of the total weight of the composition.

For its part, the glycerine may be present in an amount ranging from 0.1 to 50%, such as from 1 to 10%, of the total weight of the composition.

The composition disclosed herein may be provided in any of the galenic forms normally used in the cosmetic and dermatological fields, and it may be in the form of an optionally gelled solution, an optionally biphasic lotion-type dispersion, an emulsion obtained by dispersing a fatty phase in an aqueous phase [oil-in-water (O/W) or conversely water-in-oil (W/O)], or of a triple emulsion [water-in-oil-in-water (W/O/W) or oil-in-water-in-oil (O/W/O)], or of an ionic or nonionic vesicular dispersion. These compositions may be prepared according to the customary methods. In certain embodiments disclosed herein, the composition is in the form of an oil-in-water emulsion.

This composition may be fluid to a greater or lesser degree and may have the appearance of a white or colored cream, an ointment, a milk, a lotion, a serum, a paste or a foam. It can be optionally applied in the form of an aerosol. It can also be provided in solid form, such as in stick form. It can be used as a care product and/or as a make-up product for the skin.

The composition disclosed herein may also comprise the usual adjuvants in the cosmetic field, such as hydrophilic gelling agents, lipophilic gelling agents, hydrophilic active agents, lipophilic active agents, preservatives, antioxidants, solvents, perfumes, fillers, sunscreens, pigments, odor absorbers, and colorants. The quantities of these various adjuvants are those conventionally used in the field considered, and may, for example be present in an amount ranging from 0.01 to 20% of the total weight of the composition. These adjuvants, depending on their nature, may be introduced into the fatty phase, into the aqueous phase, or into lipid vesicles. In any case, these adjuvants, and their proportions, are chosen so as not to hamper the desired properties of the at least one (dihydro)jasmonic acid derivatives disclosed herein.

When the composition disclosed herein is an emulsion, the amount of fatty phase present may range from 5 to 80% by weight, such as from 5 to 50% by weight relative to the total weight of the composition. The oils, emulsifiers, and coemulsifiers used in the composition in the form of an emulsion may be chosen from those conventionally used in the cosmetic field. The emulsifier and coemulsifier may be present in the composition in an amount ranging from 0.3 to 30% by weight, such as from 0.5 to 20% by weight relative to the total weight of the composition.

As oils which can be used in the invention, mention may be made of mineral oils (e.g., liquid paraffin), oils of plant origin (e.g., avocado oil, soybean oil), oils of animal origin (e.g., lanolin), synthetic oils (e.g., perhydrosqualene), silicone oils (e.g., cyclomethicone) and fluorinated oils (e.g., perfluoropolyethers). It is also possible to use, as fat, fatty alcohols (e.g., cetyl alcohol), fatty acids, and waxes (e.g., carnauba wax, ozokerite).

As emulsifiers and coemulsifiers which can be used according to certain embodiments disclosed herein, mention may be made of, for example, fatty acid esters of polyethylene glycol such as PEG-100 stearate and fatty acid esters of glycerol such as glyceryl stearate.

As hydrophilic gelling agents, mention may be made of carboxyvinyl polymers (e.g., carbomers), acrylic copolymers such as acrylate/alkyl acrylate copolymers, polyacrylamides, polysaccharides, natural gums, and clays. As lipophilic gelling agents, mention may be made of modified clays such as bentones, dextrin palmitate, and hydrophobic silica.

Certain embodiments will now be illustrated by the following nonlimiting examples. In these examples, the quantities are indicated as a percentage by weight. Other than in the examples, or where otherwise indicated, all numbers expressing quantities of ingredients, reaction conditions, and so forth used in the specification and claims are understood as being modified in all instances by the term "about." Accordingly, unless indicated to the contrary, the numerical parameters set forth in the following specification and attached claims are approximations that may vary depending upon the desired properties sought to be obtained herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific examples are reported as precisely as possible. Any numerical values, however, inherently contain certain errors necessarily resulting from the standard deviation found in their respective testing measurements.

EXAMPLES

Example 1

Preparation of (1R,2R)-(±)3-methoxy-2-[(2Z)-2-pentyl]cyclopentaneacetic acid

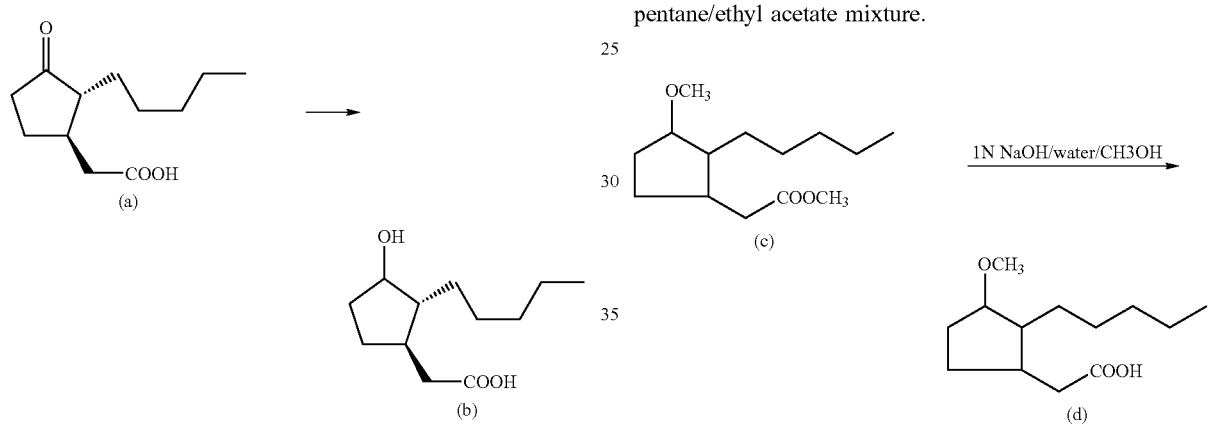

In a 50 ml three-necked flask equipped with a condenser, a thermometer and with magnetic stirring, 1 g (4.8 mmol) of (±)-dihydrojasmonic acid (a) was dissolved in 15 ml of absolute ethanol. 430 mg (11.4 mmol) of sodium borohydride $NaBH_4$ were added. The mixture was stirred for 4 hours at 50° C. Once the reaction was complete, 5 ml of water were slowly added. The precipitate formed was filtered. The filtrate was acidified with hydrochloric acid to a pH of 5 and then extracted with ethyl acetate (3×30 ml). The organic phase was dried over sodium sulphate, filtered on filter paper and then concentrated. The oil obtained was purified by chromatography on silica gel (eluent: dichloromethane/methanol). The oil obtained was dried under vacuum.

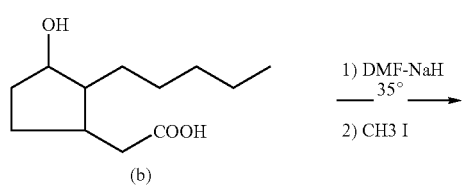

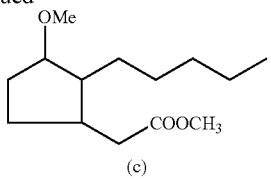

In a round-bottomed flask, 2.6 g of compound (b) were solubilized in 35 ml of dimethylformamide. 1.2 g of sodium hydride in suspension at 60% in oil were then added, the mixture was left to react for one hour at 35° C., and then 1.8 ml of methyl iodide were added. The mixture was left to react overnight at 35° C. After concentrating the reaction medium in a rotary evaporator, the residue was taken up in water and then extracted with dichloromethane. The organic phases were washed with water, and then dried over sodium sulphate. After evaporating to dryness, 3 g of oil were obtained. This product (c) was purified by column chromatography (silica gel), the elution being carried out using a pentane/ethyl acetate mixture.

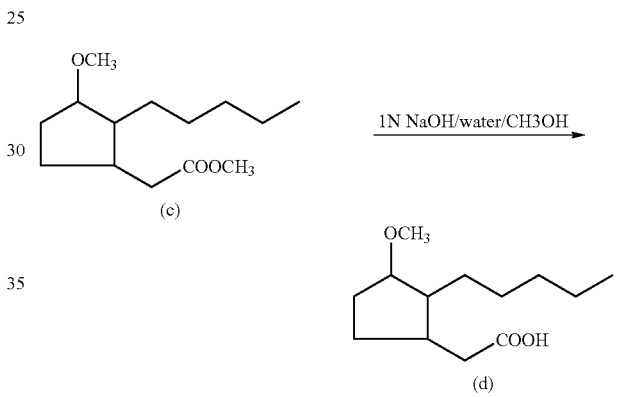

In a round-bottomed flask, 0.4 mg of compound (c) was solubilized in a mixture of 3 ml of 1N sodium hydroxide and 3 ml of methanol. After stirring overnight at room temperature, the methanol was evaporated. The remainder of the dilute aqueous phase was washed with ethyl acetate. The pH of the aqueous phase was adjusted to 2 with a 1N hydrochloric acid solution, and then washed three times with ethyl acetate. The combined organic phases were washed with water, and then dried over sodium sulphate. After evaporating to dryness, 0.25 g of oil were obtained. The yield was 65%. The NMR and mass spectra were in accordance with the expected structure for the product (d).

Example 2

Demonstration of the Desquamating Properties

The desquamating power of the compound prepared in Example 1 above was studied. This test comprised counting the corneocytes released after incubating batches of stratum corneum, isolated by trypsin/heat from plastic surgery operations, in the presence of the test compound.

Discs of stratum corneum 4 mm in diameter were cut out with a punch and placed at the bottom of a 96-well plate. Two different stratum corneum samples were used.

A solution was prepared comprising 1% by weight of compound of Example 1 in a PBS buffer supplemented at 0.1% with Triton X100. The pH of the solution was readjusted to 7.4.

50 microliters of test solution or of control solution (PBS buffer supplemented at 0.1% with Triton X100) were added to each well. The experiment was repeated three times. The mixture was incubated at 37° C., with stirring, for 24 hours.

10 microliters of solution were then collected and placed in a Mallassez cell. The corneocytes released were counted under a microscope.

The following results were obtained, which express the mean, for the three trials, of the number of corneocytes released per microliter. The corneocyte fragments were not counted.

|  | Mean (3 trials per sample) | |
| --- | --- | --- |
|  | Sample No. 1 | Sample No. 2 |
| Compound of Example 1 | 17 ± 6 | 16 ± 6 |
| Control | 6 ± 1 | 6 ± 2 |

The number of corneocytes released after incubating the isolated stratum corneum with the compound disclosed herein was much higher than the number released in the presence of buffer alone.

Example 3

Cosmetic Composition

The composition was prepared in a conventional manner for persons skilled in the art. The quantities were indicated as percentages by weight.

| Compound of Example 1 | 0.001% |
| --- | --- |
| Methylparaben | 0.1% |
| Propylparaben | 0.1% |
| Lanolin | 5% |
| Liquid paraffin | 4% |
| Sesame oil | 4% |
| Cetyl alcohol | 5% |
| Glyceryl monostearate | 2% |
| Triethanolamine | 1% |
| Propylene glycol | 5% |
| Carbomer 940 | 0.1% |
| Water | qs 100% |

What is claimed is:

1. A method for desquamating skin comprising applying to the skin at least one (dihydro)jasmonic acid compound chosen from compounds of formula (I):

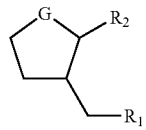

wherein:
G is a group CH—ORa,
Ra is a linear or branched $C_1$-$C_6$ hydrocarbon radical; $R_1$ is a radical —COOH; and
$R_2$ is an unsubstituted, saturated or unsaturated, linear or branched hydrocarbon radical having 5 carbon atoms;
and the, stereoisomers, thereof.

2. A cosmetic method for smoothing the visible and/or tactile irregularities of the skin surface, comprising topically applying, to the skin, a composition comprising, in a physiologically acceptable medium, glycerine; and
at least one (dihydro)jasmonic acid compound of formula (I),

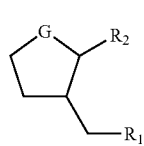

wherein:
G is a group CH—ORa,
Ra is a linear or branched $C_1$-$C_6$ hydrocarbon radical; $R_1$ is a radical —COOH; and
$R_2$ is an unsubstituted, saturated or unsaturated, linear or branched hydrocarbon radical having 5 carbon atoms;
and the, stereoisomers, thereof.

3. The method according to claim 2, wherein the method is for smoothing the wrinkles and fine lines and/or the skin spots and/or smoothing the skin.

4. The method according to claim 2, wherein the composition is applied to the skin of human subjects having a sebum level on the forehead greater than 100 µg/cm².

5. The method according to claim 1, wherein G is CH—OCH₃, $R_1$ is a radical —COOH; and $R_2$ is an n-pentyl radical.

6. The method according to claim 2, wherein G is CH—OCH₃, $R_1$ is a radical —COOH; and $R_2$ is an n-pentyl radical.

* * * * *

UNITED STATES PATENT AND TRADEMARK OFFICE
CERTIFICATE OF CORRECTION

| | | |
|---|---|---|
| PATENT NO. | : 7,365,097 B2 | Page 1 of 1 |
| APPLICATION NO. | : 10/899398 | |
| DATED | : April 29, 2008 | |
| INVENTOR(S) | : Michel Neuwels et al. | |

It is certified that error appears in the above-identified patent and that said Letters Patent is hereby corrected as shown below:

In claim 1, column 12, line 17, "the, stereoisomers, thereof." should read --the stereoisomers thereof.--.

In claim 2, column 12, line 41, "the, stereoisomers, thereof." should read --the stereoisomers thereof.--.

Signed and Sealed this

Twelfth Day of August, 2008

JON W. DUDAS
*Director of the United States Patent and Trademark Office*